United States Patent [19]

Inoue et al.

[11] Patent Number: 4,675,430
[45] Date of Patent: Jun. 23, 1987

[54] 2-ALKANOYLOXY-3-(N-OCTADECYLCARBAMOYLOXY)PROPYL 2-TRIMETHYLAMINOETHYL PHOSPHATE

[75] Inventors: Keizo Inoue, Tokyo; Hiroaki Nomura; Tetsuya Okutani, both of Osaka, all of Japan

[73] Assignee: Takeda Chemical Industries, Inc., Osaka, Japan

[21] Appl. No.: 875,701

[22] Filed: Jun. 18, 1986

[30] Foreign Application Priority Data

Jul. 15, 1985 [JP] Japan ................................ 60-156820

[51] Int. Cl.$^4$ .............................................. C07F 9/09
[52] U.S. Cl. .................................................... 558/172
[58] Field of Search .......................................... 558/172

[56] References Cited

U.S. PATENT DOCUMENTS 4,408,052 10/1983 Hozumi et al. ...................... 546/22
4,552,869 11/1985 Lautenschlager et al. ......... 558/172
4,576,933 3/1986 Tsushima et al. ..................... 514/77
4,610,979 9/1986 Lautenschlager et al. ......... 558/172

FOREIGN PATENT DOCUMENTS 1583661 1/1981 United Kingdom .

OTHER PUBLICATIONS

Cusack, Nature, vol. 285, p. 193, (May 22, 1980).
Hadváry et al., Thrombosis Research, vol. 30, pp. 143–156 (1983).
Central Patents Index, Basic Abstracts Journal, Section B: Farmdoc, Toya 22.06.78 J55002-636 (Apr. 9, 1980).

Primary Examiner—Anton H. Sutto
Attorney, Agent, or Firm—Wegner & Bretschneider

[57] ABSTRACT

2-Alkanoyloxy-3-(N-octadecylcarbamoyloxy)propyl trimethylammonioethyl phosphates and a salt thereof exhibit inhibitory activity against multiplication of tumor cells, and are useful as an antitumor agent.

2 Claims, No Drawings

2-ALKANOYLOXY-3-(N-OCTADECYLCAR-BAMOYLOXY)PROPYL 2-TRIMETHYLAMINOETHYL PHOSPHATE

TECHNOLOGICAL FIELD

This invention relates to 2-alkanoyloxypropane derivatives useful as medicines. More specifically, the present invention relates to 2-lower alkanoyloxy-3-(N-octadecylcarbamoyloxy)propyl 2-trimethylammonioethyl phosphate, i.e. a compound representable by the formula:

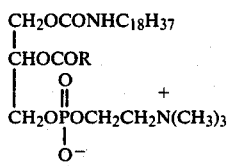

[wherein R stands for a lower alkyl group having 1 to about 3 carbon atoms], and a salt thereof.

BACKGROUND ART

As a natural phospholipid compound, there has been known platelet-activating factor (PAF) representable by the formula:

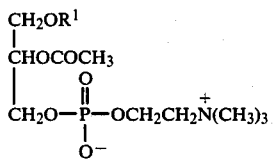

[wherein $R^1$ stands for hexadecyl or octadecyl]. Synthetic phospholipid compounds resembling the compound (II) are known to have PAF-like actions such as platelet-activating action, neutrophil activating activity, tissue-impairing action, vascular-permeability increasing action, hypotensive action or the like, though some differences in the strength of these actions of the respective compounds due to the structural differences are observed. On the other hand, as a derivative of natural phosphatidyl choline, there has been known the synthetic phospholipid compound representable by the formula:

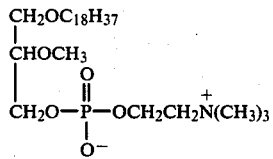

[e.g. Japanese Unexamined Patent Publication No. 52-134027 (1977)]. This compound (III) has, unlike natural phospholipid compounds, an anti-tumor activity as well as platelet aggregation activity [D. J. Hanahan et al., Biochem.Biophys. Res. Commun. 99, 183 (1981)].

This sort of action against platelets reises concern about serious circulatory disturbances such as cerebal thrombosis and angina pectoris.

The compound (III) has been recognized to show a hypotensive action and also an action of local irritation and/or damage. These actions are side actions which prevent the compound (III) from being used it as a medicine. In some of the references concerned [e.g. Thrombosis Research 30, 143 (1983)], there is disclosed a phospholipid compound of the formula:

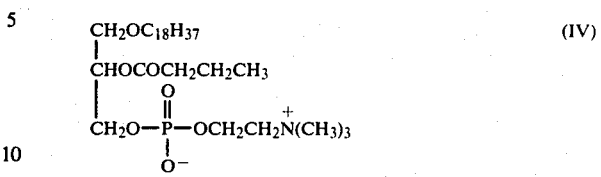

but this compound also shows platelet aggregation action.

As further examples of phospholipid compounds structurally resembling those of the formula (I), there are mentioned compounds which are included in the claims of Japanese Unexamined Patent Publication No. 58-192825 (1983). Among them, however, the compound shown by the formula

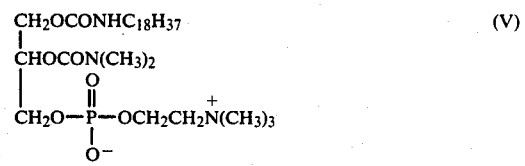

having a carbonyl group introduced at the 2-position, also shows platelet aggregation action, and thus the use of the compound as a medicine is restricted to some extent.

As described above, synthetic phospholipid compounds having a relatively small substituent at 2-position show PAF-like actions, and the use of them as medicines leaves problems to be solved because of the afore-mentioned reasons.

While a compound of the formula

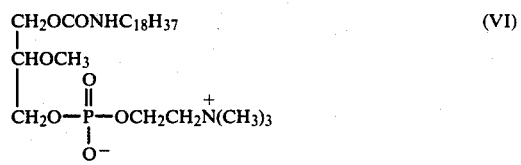

is disclosed in Japanese Unexamined Patent Publication No. 58-35194 (1983), the antitumor effect of this compound (VI) can hardly be considered sufficient.

Synthetic phospholipids, especially those which have relatively small substituents at the 2-position, in general, show actions as mentioned above, such as platelet aggregation action, hypotensive action, etc. These actions, when synthetic phospholipids are used as anti-tumor agents, are undesirable side-actions. Furthermore, the effective dose as antitumor agent is quite near the amount of causing those side actions. Therefore, these synthetic phospholipid compounds are extremely difficult to be used as anti-tumor agents as they are. For separation of the antitumor effect from the PAF activities such as platelet aggregation, hypotensive action, etc., the present inventors made extensive studies and researches. As the result, the present inventors found out that the phospholipid compounds representable by the formula (I) showed substantially no action due to the PAF action, more specifically, disappearance of platelet aggregation and remarkable weakening of hypotensive actions, while they show remarkable antitumor actions.

Thus, the present inventors found that the difference between the dose for exerting anti-tumor effect and the amount of causing the side-actions was remarkably enlarged, and also that the compound (I) of this invention had an effect of inhibition against proliferation of myeologenous leukemia HL-60 as well as differentiation inducing activity, to lead to the completion of the present invention.

DISCLOSURE OF THE INVENTION

The present invention is to provide 2-lower alkanoyloxy-3-(N-octadecylcarbamoyloxy)propyl 2-trimethylammonioethyl phosphates (I) and its salts.

The above-mentioned lower alkanoyloxy group is exemplified by alkanoyloxy groups having about 2-4 carbon atoms, such as acetyloxy, propionyloxy, butyryloxy, etc., and, among them, the acetyloxy group is preferable.

The compound (I) has two types of stereoisomers having R-configuration and S-configuration with respect to the 2-position in the glycerol structure, and compounds of each type, a mixture thereof and corresponding racemic compounds are all included in the present invention.

The compound (I) may sometimes exist in the form of e.g. a salt representable by the formula:

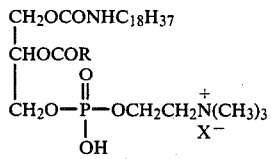
(Ia)

[wherein $X^-$ stands for an anion such as chlorine ion, bromine ion, iodine ion, etc.], or a salt representable by the formula:

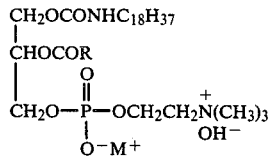
(Ib)

[wherein $M^+$ stands for alkali metal (e.g. Na, K) ion or alkaline earth metal (e.g. Ca, Mg) ion], and as such salts are preferable pharmaceutically acceptable ones.

The compound (I) of the present invention can be prepared by, for example, the following method.

A compound representable by the formula:

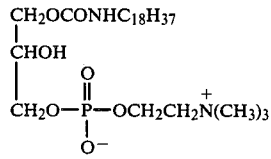
(VII)

is prepared [by the method disclosed in Japanese Unexamined Patent Publication No. 58-192825 (1983), or by a method analogous thereto], then the compound (VII) is allowed to react with a compound representable by the formula:

$$(RCO)_2O \qquad (VIII)$$

[wherein R is of the same meaning as defined above] in an inert solvent under anhydrous conditions to give the compound (I). This reaction is conducted in the presence of a tertiary amine (e.g. pyridine, triethylamine, etc.) to bring about a preferable result.

The compound (I) can also be produced by the following method: The compound (VII) is allowed to react with a compound representable by the formula:

$$RCOOH \qquad (IX)$$

[wherein R is of the same meaning as defined above] in an inert solvent under anhydrous conditions in the presence of a tertiary amine (pyridine, 4-dimethylaminopyridine, triethylamine, etc.) and a condensing agent (e.g. dicyclohexylurea, 1-ethyl-3-[3-(dimethylamino)propyl]-carbodiimide hydrochloride, etc.) to give the compound (I).

In the foregoing are described typical methods of preparing the compound (I), but methods are not limited thereto.

The compound (I) and a salt thereof can be used as a pharmaceutical composition in a powdery form or in combination with a pharmaceutically acceptable carrier or excipient.

When the compound (I) is used as an antitumor agent, it is formulated into various pharmaceutical compositions such as injections, tablets, capsules, liquids, ointments, etc., which can safely be administered non-orally or orally.

Formulation into injections or those for instillation can be conducted in accordance with a conventional method, for example, by using physiological saline or an aqueous solution containing glucose or other adjuvants. Tablets, capsules, etc. can also be prepared by conventional methods. Dosage forms of these pharmaceutical compositions vary with the purposes of administration, and, in case of injections for example, the administration route can be suitably selected from, for example, intravenous or subcutaneous route or direct administration to regional sites.

Compound (I), in which undersirable side actions (e.g. platelet aggregation, hypotension, vascular-permeability increase, tissue-impairment) are remarkably decreased or disappear while intended activities (e.g. antitumor action) are enhanced, can be safely administered as an antitumor agent against tumor-carrying warm-blooded animals. Methods, routes and dosages of administration can be suitably selected depending on the subjects to be treated and symptoms. A dose to tumor-carrying warm-blood animals is usually about 0.1 to 150 mg/kg (body weight) and preferably about 2 to 50 mg/kg (body weight) in terms of the compound (I). The said compound (I) can be administered about 1 to 3 times daily or every 2 to 7 days. For maintaining the concentration of the drug in tissue at a necessary level for a prolonged time, the compound (I) can be infused intravenously for a long time.

The present invention is illustrated in further detail by way of the following Examples and Examples of Pharmaceutical Preparation, but it is not to be limited thereto.

EXAMPLE 1

2-(Acetoxy)-3-(N-octadecycarbamoyloxy)propyl 2-trimethylammonioethyl phosphate.

In 10 ml of pyridine was suspended 200 mg of 2-(hydroxy)-3-(N-octadecylcarbamoyl)propyl 2-trimethylammonioethyl phosphate. To the suspension was added 1 ml of acetic anhydride. The mixture was stirred at room temperature for 4 days, followed by removing the solvent under reduced pressure. The residue was subjected to silica gel (3 g) column-chromatography, followed by elution with methanol. The fractions containing the desired compound were combined and concentrated. To the concentrate was added a small volume of acetone to solidify the desired compound, which was collected by filtration and dried to obtain 126 mg of colorless solid (yield 56). Thin-layer chromatography [silica-gel, chloroform-methanol-water (65:25:4)]Rf=0.22 single spot IR (KBr)cm$^{-1}$: 3400, 2930, 2860, 1740, 1710, 1240, 1095, 1080, 975.

NMR (90 MHz, CDCl$_3$)δ: 0.87 (3H), 1.26 (30H), 1.46 (2H), 2.05 (3H), 3.10 (2H), 3.30 (9H), 3.6 0–4.35 (8H), 5.13 (1H), 5.80 (1H).

EXAMPLE 2

3-(N-octadecylcarbamoyloxy)-2-(propionyloxy)propyl 2-trimethylammonioethyl phosphate In 8 ml of pyridine was dissolved 600 mg. of 2-(hydroxy)-3-(N-octadecylcarbamoyloxy)propyl 2-trimethyl-ammonioethyl phosphate. To the solution was added 1.3 ml of propionic anhydride.

The mixture was stirred at room temperature for 24 hours, followed by addition of 8.7 ml of propionic anhydride and 10 ml of propionic acid. The mixture was stirred at room temperature for 27 hours. The reaction mixture was concentrated under reduced pressure. To the residue was added 20 ml of carbon tetrachloride, followed by concentration to dryness under reduced pressure. To the residue was added 10 ml of acetone to solidify the desired compound, which was collected by filtration and dried to obtain 480 mg of colorless solid (yield 72.6%).

Thin-layer chromatography [silica-gel, chloroform-methanol-water (65:25:4) Rf=0.36 single spot IR (KBr)cm$^{-1}$: 3420, 2920, 2850, 1730, 1705, 1540, 1465, 1240, 1090, 1060, 970.

NMR (90 MHz, CDCl$_3$—CD$_3$OD)δ: 0.87 (3H), 1. 12 (3H), 1.26 (30H), 1.47 (2H), 2.35 (2H), 3.09 (2H), 3.28 (9H), 3.75 (2H); 4.01–4.27 (6H), 5.18 (1H).

EXAMPLE 3

2-(Butyryloxy)-3-(N-octadecylcarbamoyloxy)propyl 2-trimethylammonioethyl phosphate A mixture of 875 mg of 2-(hydroxy)-3-(N-octadecylcarbamoyloxy)propyl 2-trimethylammonioethyl phosphate, 30 ml of pyridine, 10 g of butyric anhydride and 10 g of butyric acid was stirred at room temperature for 24 hours. To the mixture was added 10 ml of methanol, which was left standing at room temperature for 4 hours, followed by removing materials of low boiling points by distillation under reduced pressure. The residue was subjected to silica gel (10 g) column chromatography. Elution with chloroform-methanol-water (65:25:4) gave 497 mg of the above-titled compound as colorless powder.

(Yield 51%)

Thin-layer chromatography [silica-gel, chloroform-methanol-water (65:25:4)]Rf=0.38 single spot IR (Nujol)cm$^{-1}$: 1725, 1695, 1535, 1260, 1250, 1090, 1070, 1050, 970.

NMR (60 MHz, CDCl$_3$—CD$_3$OD)δ: 0.90 (3H), 0.97 (3H), 1.20–1.83 (34H), 2.30 (2H), 3.20 (11H), 3.50–3.70 (2H), 3.90–4.47 (6H), 5.00–5.40 (1H).

EXAMPLE OF PHARMACEUTICAL PREPARATION 1

In 1.0 l of distilled water was dissolved 50 g of the compound obtained in Example 1. The solution was subjected to aseptical filtration.

One (1) ml each portion of the filtrate was distributed to 1000 vials under sterile conditions. These vials were subjected to freeze-drying, then tightly sealed.

On the other hand, 2 ml each portion of 2 l of distilled water for injection containing 100 g of mannitol was aseptically distributed to 1000 ampoules for injection. These ampoules were subjected to melt-sealing.

When used, the powder contained in one vial is dissolved in the mannitol solution for injection.

EXAMPLE OF PHARMACEUTICAL PREPARATION 2

| Tablet | |
|---|---|
| (1) Compound of Example 3 | 100 mg |
| (2) Lactose | 200 mg |
| (3) Corn starch | 51 mg |
| (4) Hydroxypropyl cellulose | 9 mg |

The above ingredients (1) to (4) are mixed and granulated. The granules are mixed with corn starch (8 mg) and magnesium stearate (2 mg), and the mixture is compressed on a tabletting machine to give a 370 mg tablet of 9.5 mm diameter.

EXAMPLE OF PHARMACEUTICAL PREPARATION 3

The tablet prepared in the above Example of Pharmaceutical Preparation 2 is coated with an acetone-ethanol (4:6) mixture dissolving hydroxypropylmethyl methyl cellulose phthalate (14 g) and castor oil (1 mg) at a concentration of 7% to give an enteric coated tablet.

TEST EXAMPLE 1

Antitumor activity of 2-(acetoxy)-3-(octadecylcarbamoyloxy)propyl 2-trimethylammonioethyl phosphate (Example 1)

$1 \times 10^5$ Sarcoma 180 cells per mouse were intraperitoneally transplanted into ICR mice (5 heads in one group). Each of these mice was injected intraperitoneally with 0.33 mg/mouse of the compound obtained in Example 1 dissolved in physiological saline, three times, i.e. once daily for 3 days starting 1 hour after the transplantation of the cells. On the other hand, the reference compounds (III), (V), and (VI) were respectively administered under the same conditions to groups to be compared. Life prolongation rates of mice which died in test groups against the control group to which no drug was administered and the number of animals surviving on the 60th day after starting the experiment are shown in Table 1.

TABLE 1

| Test compound | Life Prolongation Rate (T/C %) | Number of Surviving Animals/Number of Test Animals |
|---|---|---|
| Compound of Ex. 1 | 274 | 3/5 |
| Compound (III) | 162 | 0/5 |
| Compound (V) | 116 | 0/5 |

TABLE 1-continued

| Test compound | Life Prolongation Rate (T/C %) | Number of Surviving Animals/Number of Test Animals |
|---|---|---|
| Compound (VI) | 152 | 1/5 |
| Control | 100 | 0/5 |

TEST EXAMPLE 2

C3H/He mice (5 heads in one group) were administered intraperitoneally with 0.25 mg/mouse of the drug continuously for 4 days. On the 6th day, each mouse was injected intraperitoneally with $1 \times 10^4$ MM46 cells, followed by injecting 0.25 mg/mouse of the respective drug once daily for 4 days from one day after the next day of the injection of the cells. On the other hand, the control compounds (III) and (VI) were respectively administered under the same conditions to groups to be compared. Life prolongation rates relative to those of the control group to which no drug was administered and the number of animals surviving on the 60th day after injection of MM46 are shown in Table 2.

TABLE 2

| Test compound | Life Prolongation Rate (T/C %) | Number of Surviving Animals/Number of Test Animals |
|---|---|---|
| Compound of Ex. 1 | — | 5/5 |
| Compound (III) | 137 | 3/5 |
| Compound (VI) | 107 | 3/5 |
| Control | 100 | 0/5 |

TEST EXAMPLE 3

Activity on Platelet
[Test Method and Result]

Blood was collected from a male rabbit by using an injection syringe containing 3.15% citric acid (blood: 3.15% citric acid = 9:1) as an anti-coagulant. The blood thus collected was subjected to centrifugation at 1000 rpm for 10 minutes to obtain platelet rich plasma (PRP). The PRP was further centrifuged at 1400 rpm for 15 minutes to obtain platelet pellet, which was suspended in $Ca^{++}$.free Tyrode (containing 0.25% of gelatin) to prepare washed PRP. At 37° C., 250 μl of this washed PRP was stirred for 2 minutes, to which was added 25 μl of $Ca^{++}$ solution of 0.2 to 0.5 mM. The mixture was stirred for further 30 seconds. To the resultant was added each of the respective test drugs to prepare test solutions of given concentrations. Aggregation of the platelet was determined by means of aggregometer (manufactured by Rikadenki). The results are shown by Table 3.

TEST EXAMPLE 4

Seven weeks old male Sprague Dawley rats (200 to 290 g) were anesthetized by intraperitoneal injection of pentobarbital sodium salt (60 mg/kg). Cannules were inserted at the left carotid artery (for measurement of blood pressure) and left femoral vein (for intravenous administration).

A given amount of each of the test compounds was administered to determine the drop of blood pressure (Δ mmHg). The results are shown by Table 3.

TABLE 3

| Test Drugs | Platelet Aggregation Activity (%) Test Concentration (M) | | | Hypotensive activity (ΔmmHg) Dosage (μg/kg) | | | |
|---|---|---|---|---|---|---|---|
| | $1 \times 10^{-8}$ | $2 \times 10^{-6}$ | $3 \times 10^{-5}$ | 0.3 | 1 | 30 | 300 |
| Compound of Ex. 1 | — | — | 0 | — | — | — | −6 |
| Compound (II)* | 73.1 | — | — | −28 | −50 | — | — |
| Compound (III)** | — | 0 | 45.5 | — | — | 0 | −43 |
| Compound (V) | — | 6.3 | 75.7 | — | — | −9 | −26 |

*$R^1 = C_{18}H_{37}$
**Racemic Compound

TEST EXAMPLE 5

$1 \times 10^4$ MM46 cells per mouse were intraperitoneally transplanted into C3H/He mice (8-weeks old, 5 animals in one group). Starting from the second day after the transplantation, 0.25 mg/mouse of the drug was intraperitoneally injected to the animals once daily for 4 days consecutively. The reference compound (III) was administered under the same conditions. Life prolongation rates of the dead mice in the test group against the control group to which no drug was administered and the number of animals surviving on 36th day after starting the experiment are shown in Table 4.

TABLE 4

| Test Drug | Life Prolongation Rate* (T/C %) | Number of Surviving Animals/Number of Test Animals |
|---|---|---|
| Compound of Ex. 1 | — | 5/5 |
| Compound (III) | 136 | 1/5 |
| Control | 100 | 0/5 |

*Life prolongation rate calculated based on only died mice.

What is claimed is:

1. A compound of the formula:

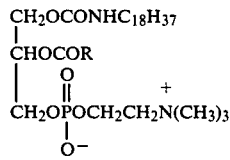

wherein R stands for an alkyl group having 1 to 3 carbon atoms, or a pharmaceutically acceptable salt thereof.

2. A compound according to claim 1, which is 2-(acetoxy)-3-(N-octadecylcarbamoyloxy)propyl 2-trimethylammonioethyl phosphate.